(12) United States Patent
Fleury Rey et al.

(10) Patent No.: US 11,812,755 B2
(45) Date of Patent: Nov. 14, 2023

(54) FLAVOUR GENERATION IN FOOD (71) Applicant: SOCIÉTÉ DES PRODUITS NESTLÉ S.A., Vevey (CH)

(72) Inventors: Yvette Fleury Rey, Ursy (CH); Christina Vafeiadi, Lausanne (CH); Stephane Duboux, St-Prex (CH); Catherine Ngom-Bru, Montpreveyres (CH); Clementine Tastet, Palezieux (CH); Cassandra Mokdad, Epalinges (CH); Christof Gysler, Blonay (CH); Carl Erik Hansen, Epalinges (CH)

(73) Assignee: Societe des Produits Nestle S.A., Vevey (CH)

( * ) Notice: Subject to any disclaimer, the term of this patent is extended or adjusted under 35 U.S.C. 154(b) by 94 days.

(21) Appl. No.: 16/301,659

(22) PCT Filed: May 16, 2017

(86) PCT No.: PCT/EP2017/061702
§ 371 (c)(1),
(2) Date: Nov. 14, 2018

(87) PCT Pub. No.: WO2017/198652
PCT Pub. Date: Nov. 23, 2017

(65) Prior Publication Data
US 2019/0281839 A1 Sep. 19, 2019

(30) Foreign Application Priority Data
May 19, 2016 (EP) .................................... 16170473

(51) Int. Cl.
A21D 8/04 (2006.01)
A23L 27/21 (2016.01)
(Continued)

(52) U.S. Cl.
CPC ............. A21D 8/042 (2013.01); A21D 13/45 (2017.01); A23L 5/25 (2016.08); A23L 27/215 (2016.08);
(Continued)

(58) Field of Classification Search
CPC ......... A23L 5/25; A23L 27/215; A21D 8/042; A21D 13/45; C12Y 304/11005;
(Continued)

(56) References Cited

U.S. PATENT DOCUMENTS

2003/0186420 A1* 10/2003 Ito ............................ C12N 9/48
435/226
2004/0156980 A1* 8/2004 Fleury Rey .............. A21D 2/00
426/656

FOREIGN PATENT DOCUMENTS

JP 07115969 5/1995
JP 2012213376 11/2012
(Continued)

OTHER PUBLICATIONS

JPH0715969—machine translation of desription (Year: 1995).*
(Continued)

Primary Examiner — Subbalakshmi Prakash
(74) Attorney, Agent, or Firm — K&L Gates LLP (57) ABSTRACT The present invention relates to flavour generation. In particular the invention relates to a method for flavour generation in a heat-treated food product using a prolidase enzyme. The invention also relates to a heat-treated food product prepared according to the method of the invention.

8 Claims, 6 Drawing Sheets

Specification includes a Sequence Listing.

(51) Int. Cl.
  *A21D 13/45* (2017.01)
  *A23L 5/20* (2016.01)
  *C12N 9/48* (2006.01)
  *C12N 15/52* (2006.01)

(52) U.S. Cl.
  CPC .......... *C12Y 304/11005* (2013.01); *C12Y 304/13009* (2013.01); *A23V 2002/00* (2013.01); *C12N 9/485* (2013.01); *C12N 15/52* (2013.01)

(58) Field of Classification Search
  CPC .......... C12Y 304/13009; C12N 15/52; C12N 9/485; A23V 2002/00
  USPC .......... 426/18
  See application file for complete search history.

(56) References Cited

FOREIGN PATENT DOCUMENTS

| WO | 9426882 | 11/1994 | |
|----|---------|---------|---|
| WO | WO-2005117595 A1 * | 12/2005 | ............. A21D 8/042 |

OTHER PUBLICATIONS

Unknown "SubName: Full=Dug1p{ECO:0000313|EMBL:AJU35769.1}; LIKKEANGYF KGVDAVCISD NYWLGTKKPV LTYGLRGCNY YQTIIEGPSA DLHSGIFGGV"Retrieved from EBI accession No. UNIPROT:A0A0D4JDQ1, May 27, 2015, 1 page, XP002761156.

Hofmann, Influence of L-Cysteine on the Formation of Bitter-Tasting Aminohexose Reductones from Glucose and L-Proline: Identification of a Novel Furo[2,3-b]thiazine, J. Agric. Food Chem., vol. 47, Issue No. 11, 1999, pp. 4763-4768.

Database WPI Week 199527, Derwent World Patents Index; AN 1995-202831, XP002761157,1 page.

European Office Action for Appl No. 17 729 379.2—1106 dated Jun. 16, 2020.

Uniprot, Apr. 13, 2016, pp. 1-4.

Yaron et al., "Proline-Dependent Structural and Biological Properties of Peptides and Proteins", Critical Reviews in Biochemistry and Molecular Biology, vol. 28, Issue No. 1, Jan. 1, 1993, pp. 31-81.

Xiao et al., "Maillard Reaction and it's Application in Food Flavor", Apr. 15, 2005, pp. 27-30.

Office Action Received for Application No. 201780029153.0, dated Mar. 28, 2022, 15 Pages(6 Pages of English Translation).

* cited by examiner

FLAVOUR GENERATION IN FOOD

CROSS REFERENCE TO RELATED APPLICATIONS

The present application is a National Stage of International Application No. PCT/EP2017/061702, filed on May 16, 2017, which claims priority to European Patent Application No. 16170473.9, filed on May 19, 2016, the entire contents of which are being incorporated herein by reference.

FIELD OF THE INVENTION

The present invention relates to flavour generation. In particular the invention relates to a method for flavour generation in a heat-treated food product using a prolidase enzyme. The invention also relates to a heat-treated food product prepared according to the method of the invention.

BACKGROUND OF THE INVENTION

In food, the Maillard reaction results in both the production of flavours and browning (see Bailey, M. E. (1994) Maillard reactions and meat flavour development, pages 153-173, In: Flavour of meat and meat products, Ed. F. Shahidi, Academic Press; Ames, J. M. (1992) The Maillard Reaction, pages 99-153, In: Biochemistry of Food Proteins, Ed. B. J. F. Hudson, Elsevier App. Sci. London).

With respect to flavour generation, the Maillard reaction can be broken down into four stages. The first stage involves the formation of glycosylamines. The second stage involves rearrangement of the glycosylamines to form Amadori and Heyns rearrangement products (often abbreviated in the literature to "ARPs" and "HRPs", respectively). The third stage involves dehydration and or fission of the Amadori and Heyns rearrangement products to furan derivatives, reductones and other carbonyl compounds (which may have significant organoleptic qualities). (These "third stage products" may also be produced without the formation of ARP's or HRP's. The fourth stage involves the conversion of these furan derivatives, reductones and other carbonyl compounds into coloured and aroma/flavour compounds. Thus, products and reactants present in both the third and fourth stage of the Maillard reaction contribute towards aroma/flavour.

Maillard reactions occur naturally in food, but it is also known to use Maillard reaction products to improve the flavour and aroma of foodstuffs.

Amino acids as flavour precursors have been extensively studied in combination with reducing sugars in Maillard reaction systems. Proline was described by Hodge et al. (1972, Cereal Sci Today 17: 34-40) as the key amino acid precursor for roast aroma. It was further shown by Schieberle (1990, Z Lebensm Unters Forsch 191: 206-209) that a key impact compound, 2-acetyl-1-pyrroline was generated from proline and ornithine. In U.S. Pat. Nos. 3,687,692 and 3,782,973 it was reported that proline-based reaction mixtures produced a caramel character upon heating with cyclic ketones. U.S. Pat. No. 4,022,920 disclosed that Amadori rearrangement compounds have been produced from proline and 6-deoxy-aldohexoses such as rhamnose under reflux in ethanol followed by drying. The dried mixture was incorporated into a food matrix followed by heating. Among the compounds known to be generated from proline and rhamnose are 4-hydroxy-2,5-dimethyl-3 (2H)-furanone and several 2,3-dihydr(IH)-pyrrolizines (Shaw and Ho 1989, Thermal generation of aromas, eds. Parliament T H, McGorrin R J, Ho C-T, American Chemical Society, Washington, DC; Shaw et al. 1990, Perfumer & Flavorist 15: 60-66; Tressl et al. 1985, J Agric Food Chem 33: 919-923 and J Agric Food Chem 33: 924-928).

WO2005/117595 describes the use of a proline-specific endoprotease together with an exopeptidase for improving flavour in baked cereal products. For proline-specific endoprotease enzymes that yield a peptide chain with a carboxy-terminal proline residue, WO2005/117595 suggests combining the endoprotease with the carboxypeptidase CPD-Y or a proline-specific carboxypeptidase from *Xanthomonas* or *Escherichia*. However, flavour generation is complex and subtle, with side reactions often playing an important role in the final flavour obtained. The choice of enzymes can influence the character of the flavour generated, as well as the efficiency of generation in different food matrices and conditions, even with enzymes whose primary action is similar.

WO2008/148737 describes a baked food stuff with an improved flavour which is obtained by the addition of flavour precursors (amino acids and reducing sugars) directly to ingredients which are then baked to form baked foodstuffs. Such approach allows formation of the aroma molecules even when the baking duration is short.

Regardless of the advantages provided by the inventions described above to generate flavours in baked food stuffs, they still suffer from some disadvantages.

The use of flavour precursors derived from external sources in order to generate aromas upon heating adds ingredients to the food which may not be familiar to a consumer or expected in food of that type. For example the flavour precursors may not be ingredients that the consumer would use if preparing the food themselves. Many consumer highly appreciate the generation of flavours directly from raw materials which may be used as ingredients in the food products rather than from addition of flavour precursors from external sources. Such raw materials should ideally have good consumer acceptance.

Accordingly, it is advantageous to generate such flavour precursors during the process of preparation of baked foodstuff directly from the raw materials which may be of use as ingredients of the recipe.

Where flavour precursors are generated during the processing of common raw materials it would be desirable to increase the selective production of flavour precursors which lead to attractive roast or baked flavours, for example it would be desirable to increase the selective production of free amino acids such as proline. Efficient production of target flavour precursors allows faster flavour generation processes, more intense flavour generation and avoids the generation of undesirable flavours from the generation of non-target precursors. It would also be advantageous to provide alternatives to known enzymes generating flavour precursors, allowing the formation of different flavour notes and the creation of new flavour profiles for products. Where such a flavour profile becomes associated with a branded food product it is sometimes described as a "signature flavour". Even subtle differences in flavour can be important to the success of a product.

Where enzymes are used to perform conversions of raw material, for example during the food preparation process, it is desirable that these enzymes, and the form in which they are added, have good consumer acceptability. It would be preferable to use enzymes derived from microorganisms with good consumer acceptance, for example microorganisms with a long history of use in food. Many consumers do not wish to have genetically modified microorganisms associated with the production of their food so it is advantageous to achieve the generation of flavour precursors without the use of a genetically modified microorganisms.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

An object of the present invention is to improve the state of the art and to provide a solution to overcome at least some of the inconveniences described above or at least to provide a useful alternative. The object of the present invention is achieved by the subject matter of the independent claims. The dependent claims further develop the idea of the present invention.

Accordingly, the present invention provides in a first aspect a method for flavour generation comprising; (a) contacting an edible peptide-containing material with a prolidase to form a hydrolysed preparation, wherein the prolidase comprises an amino acid sequence having at least 95% identity to SEQ ID NO:1; (b) incorporating the hydrolysed preparation obtainable from step (a) into a food preparation which comprises at least a reducing sugar; or, where the hydrolysed preparation already comprises at least a reducing sugar, the hydrolysed preparation may be the food preparation; and (c) subjecting the food preparation to heat treatment to obtain a heat-treated food product.

In a second aspect, the invention relates to a hydrolysed preparation obtainable by contacting an edible peptide-containing material with a prolidase, wherein the prolidase comprises an amino acid sequence having at least 95% identity to SEQ ID NO:1.

A third aspect of the invention relates to a food preparation comprising a prolyl endopeptidase, a prolidase, proline as free amino acid and ornithine as a free amino acid; wherein the prolidase comprises an amino acid sequence having at least 95% identity to SEQ ID NO:1; and, if methionine is present as a free amino acid, the molar ratio of proline to methionine as free amino acids is greater than 18.

Still further aspects of the invention are a heat-treated food product obtainable according to the method of the invention and the use of a prolidase comprising an amino acid sequence having at least 95% identity to SEQ ID NO:1 to improve the flavour of a heat-treated food product.

It has been surprisingly found by the inventors that particularly good baked flavours can be obtained by using a prolidase comprising an amino acid sequence having at least 95% identity to SEQ ID NO:1 to hydrolyse edible peptide-containing material and then combining with a reducing sugar and applying heat. In particular, proline can be selectively liberated from food proteins and food polypeptides in a highly efficient manner by combining a prolyl endopeptidase with a prolidase comprising an amino acid sequence having at least 95% identity to SEQ ID NO:1. When the resulting mixture is further processed by heating it in a food preparation comprising a reducing sugar, attractive flavours are produced, having baked and toasted notes. The use of a prolidase comprising an amino acid sequence having at least 95% identity to SEQ ID NO:1 surprisingly provides a particularly attractive flavour profile. Compared to the combination of a prolyl endopeptidase and the prolidase CPD-Y, a higher specificity towards proline production was surprisingly observed.

The method according to the invention presents the advantage of delivering flavour notes in heat-treated food products without the need to add amino acids as flavour precursors during the process.

DETAILED DESCRIPTION OF THE INVENTION

Consequently the present invention relates in part to a method for flavour generation (for example in a heat-treated food product) comprising; a) contacting an edible peptide-containing material with a prolidase to form a hydrolysed preparation, wherein the prolidase comprises an amino acid sequence having at least 95% identity to SEQ ID NO:1; b) incorporating the hydrolysed preparation obtainable (for example obtained) from step (a) into a food preparation which comprises at least a reducing sugar; or, where the hydrolysed preparation already comprises at least a reducing sugar, the hydrolysed preparation may be the food preparation; and (c) subjecting the food preparation to heat treatment to obtain a heat-treated food product.

The term flavour is used in the present invention to refer to the combination of taste and aroma. Taste refers to the sensation of flavour perceived in the mouth and aroma refers to perception inside the nose. Chemically, a "flavour" may be one or more taste active molecules, one or more aroma molecules, or a mixture of these. Some taste active molecules are also aroma molecules.

Within the context of the present invention, the term "heat treated food product" identifies a food product which has been subject to heat treatment. A food product is a substance that can be used or prepared for use as food. Non-limiting examples of heat treating techniques are: oven baking, roller drying, extrusion, spray drying. Non limiting examples of heat treated food products according to the present invention are:

biscuits, wafers, cereals (breakfast and infant), bread, ice-cream cones, milk powder, non-dairy beverage creamers, pizza and the like.

The term "edible" is used in the context of the present invention to mean substances which can be eaten safely. Whilst the current invention is not limited to substances permitted for consumption in any particular jurisdiction, edible compositions may for example comprise materials approved for human consumption by the U.S. Food and Drug Administration.

The peptide-containing material according to the invention may be comprise a polypeptide. The peptide-containing material according to the invention may comprise proline. The peptide-containing material may comprise a protein. Proteins consist of one or more polypeptides arranged in a biologically functional way. Preferably the peptide-containing material comprises polypeptides which have more than 10 amino acids. The peptide-containing material may be a peptone, a water-soluble mixture of polypeptides and amino acids formed by the partial hydrolysis of protein.

A prolidase is an enzyme that catalyzes the hydrolysis of the peptide bond between an amino acid and proline or hydroxyproline. In the context of the current invention the prolidase may be a proline dipeptidase, but it may also catalyse the hydrolysis of the peptide bond of larger peptides such as tripeptides or tetrapeptides that have proline as the terminal amino acid.

The prolidase may comprise an amino acid sequence having at least 97%, 98% or 99% identity to SEQ ID NO:1. The prolidase may have the amino acid sequence shown in SEQ ID NO:1.

```
                                          (SEQ ID NO: 1)
MSHSLTSVFQKIDSLKPQFFSRLTKAIQIPAVSSDESLRSKVFDKAKFIS

EQLSQSGFHDIKMVDLGIQPPPISTPNLSLPPVILSRFGSDPSKKTVLVY

GHYDVQPAQLEDGWDTEPFKLVIDEAKGIMKGRGVTDDTGPLLSWINVVD

AFKASGQEFPVNLVTCFEGMEESGSLKLDELIKKEANGYFKGVDAVCISD

NYWLGTKKPVLTYGLRGCNYYQTIIEGPSADLHSGIFGGVVAEPMIDLMQ

VLGSLVDSKGKILIDGIDEMVAPLTEKEKALYKDIEFSVEELNAATGSKT

SLYDKKEDILMHRWRYPSLSIHGVEGAFSAQGAKTVIPAKVFGKFSIRTV

PDMDSEKLTSLVQKHCDAKFKSLNSPNKCRTELIHDGAYWVSDPFNAQFT

AAKKATKLVYGVDPDFTREGGSIPITLTFQDALNTSVLLLPMGRGDDGAH

SINEKLDISNFVGGMKTMAAYLQYYSESPEN
```

Within the context of the present invention the term "hydrolysed preparation" identifies a composition based on the edible peptide-containing material and comprising any substance generated by the proteolytic action on the edible peptide-containing material of the enzymes present. If the enzymes are generated in-situ, for example by the activities of microorganisms, then the hydrolysed preparation may comprise the microorganisms and/or their residues. Within the context of the present invention, the term "microorganism" identifies a unicellular organism being a bacterium, a filamentous fungi or a yeast. The hydrolysed preparation according to the invention may comprise proline as a free amino acid.

Within the context of the present invention the term "food preparation" identifies a mixture of ingredients which is meant to deliver a "heat treated food product" when subjected to heat treatment. Non limiting examples of "food preparation" are: batters, doughs, mixtures comprising cereals and milk powder, mixtures comprising milk powder and flour, and the like. Within the context of the present invention the terms "dough" or "batter" identify a food ingredient mixture as above defined which is mainly based on cereal flour and water in different ratios. Such dough or batter may also comprise additional ingredients such as for example fats, salts, sugars, eggs, milk and the like.

Within the context of the present invention, the term "reducing sugar" identifies any sugar that either has an aldehyde group or is capable of forming one in solution through isomerisation, such aldehyde group allowing the sugar to act as a reducing agent. The reducing sugar in the current invention may be a mono or oligosaccharide, for example a mono to tetra-saccharide. The reducing sugar may be selected from the group consisting of C5 and C6 monosaccharides. The reducing sugar may be selected from the group consisting of fructose, glucose, xylose, tagatose, rhamnose, maltose, lactose, fucose, arabinose, galactose and mixtures thereof. The reducing sugar may be selected from the group consisting of fructose, glucose or rhamnose. The reducing sugar may be rhamnose.

The prolidase according to the method of the invention may be obtainable (for example obtained) from *Saccharomyces cerevisiae*. Yeasts have good consumer acceptance in food processing due to their long history of use. The prolidase according to the method of the invention may be comprised within a yeast preparation, for example a yeast preparation comprising lysed cells of *Saccharomyces cerevisiae*. The prolidase according to the method of the invention may be obtainable (for example obtained) from a modified strain of *Saccharomyces cerevisiae*. The prolidase according to the method of the invention may be obtainable (for example obtained) from *Saccharomyces cerevisiae* CNCM I-4003 or CNCM I-4006. The prolidase may be the prolidase from *Saccharomyces cerevisiae* having the UniProtKB P43616. This enzyme has the amino acid sequence shown in SEQ ID NO:1.

*Saccharomyces cerevisiae* CNCM I-4003 was deposited with the Collection Nationale de Cultures de Microorganismes (CNCM), Institut Pasteur, 25 rue du Docteur Roux, F-75724 PARIS Cedex 15, France, on 12 Jun. 2008 and given the deposit number I-4003. *Saccharomyces cerevisiae* CNCM I-4006 was deposited with the Collection Nationale de Cultures de Microorganismes (CNCM), Institut Pasteur, 25 rue du Docteur Roux, F-75724 PARIS Cedex 15, France, on 12 Jun. 2008 and given the deposit number I-4006.

The prolidase according to the method of the invention may be obtainable (for example obtained) by the lysis of *Saccharomyces cerevisiae*. The lysis may be induced by increasing the temperature of a fermentation broth comprising a temperature sensitive strain of *Saccharomyces cerevisiae* such as CNCM I-4006, the temperature increase may be accompanied by the addition of a nutrient sugar to the fermentation broth such as glucose. For example, the prolidase may be obtained by growing a temperature sensitive strain of *Saccharomyces cerevisiae* (for example CNCM I-4006) in a protein containing medium under permissive conditions to reach a concentration of at least 10 million viable cells per mL of protein containing medium and then increasing the temperature of the protein containing medium to a value between 32 to 45° C. for sufficient time to allow the *Saccharomyces cerevisiae* to at least partially lyse. Within the context of the present invention, the term "permissive conditions" for the growth of a microorganism identifies temperature and atmosphere conditions which are appropriate to allow growth of specific microorganisms, for example without leading to their even partial lysis. For example, for *Saccharomyces cerevisiae*, permissive conditions may be between 20° C. and 30° C. Where all the components of the protein containing medium are food grade, the medium and the lysed *Saccharomyces cerevisiae* cells may be incorporated into the hydrolysed preparation of the method of the invention. Indeed, the liberation of prolidase by lysis of *Saccharomyces cerevisiae* may be directly part of the food product production process, so-called "in-process" generation of enzymes.

In the case of food products it may be beneficial to introduce a yeast into the food production process rather than a pure enzyme. Including a yeast which undergoes lysis when the temperature is increased presents the operational advantage that, in the hydrolysed preparation, prolidase is delivered spontaneously and amino acid flavour precursors are generated without any need for external intervention on the medium. Such hydrolysed preparation can be thus simply incorporated into the food preparation (batter or dough for example) for its standard further processing.

Furthermore, as the structure of the heat-treated food product forms at the same time as the flavour active molecules are generated, the flavour active molecules become trapped within the food matrix and the desirable notes are strong in the finished foodstuff.

Within the context of the present invention, the term "suitable conditions" for the growth of a microorganism identifies temperature and atmosphere conditions which are appropriate to allow growth of specific microorganisms. Within the context of the present invention the term "protein containing medium" identifies a growth medium for microorganisms which comprises, micronutrients, nitrogen sources and carbon sources. If not already provided by the above mentioned nitrogen sources, the medium also incorporates sources of amino acids such as proteins, peptides or protein hydrolysates.

A method for flavour generation may comprise; a) growing at a permissive temperature and in a protein containing medium a temperature sensitive microorganism (for example *Saccharomyces cerevisiae*) which will at least partially lyse in the temperature range of about 32 to 45° C.; b) after reaching a concentration of at least 10 million viable cells per mL of protein containing medium, increasing the temperature of the protein containing medium to a value comprised between 32 to 45° C. for sufficient time to allow microorganism to at least partially lyse; c) optionally adding while performing step b) any nutrient originally comprised in in the protein containing medium and depleted during step a); d) maintaining the protein containing medium under the same conditions as per step b) for a period ranging from 1 hour to 10 days after temperature has been increased; e) incorporating the fermented preparation obtainable from step d) into a food preparation which comprises at least a reducing sugar; f) subjecting the food preparation to heat treatment to obtain a heat-treated food product.

In one embodiment of the method of the invention, the edible peptide-containing material is contacted with a prolyl endopeptidase in addition to a prolidase. For example, the edible peptide-containing material may be contacted with a prolyl endopeptidase before, or simultaneously with being contacted with the prolidase. The prolyl endopeptidase may be a proline-specific endoprotease that yields a peptide chain with a carboxy-terminal proline residue. The prolyl endopeptidase may be a proline-specific endoprotease from *Aspergillus niger*, for example the prolyl endopeptidase may be Maxipro PSP or Maxipro XF from DSM.

In one embodiment, the method of the invention generates a hydrolysed preparation comprising a mixture of several free amino acids. For example, the mixture of several free amino acids generated according to the invention may comprise proline, lysine, alanine, glutamine, valine, arginine, phenyl alanine and ornithine. The mixture of several free amino acids generated in the hydrolysed preparation according to the invention may comprise proline, lysine, glutamine, phenyl alanine and ornithine. The mixture of free amino acids generated according to the invention may comprise proline, lysine, glutamine and phenyl alanine, with proline being the free amino acid with the highest molar fraction in such mixture. In an embodiment, in the mixture of free amino acids generated in the hydrolysed preparation according to the invention, asparagine may be substantially absent. In an embodiment, the mixture of free amino acids generated in the hydrolysed preparation according to the invention may comprise a mixture of free amino acids wherein proline, lysine, glutamine and phenylalanine are present at a concentration greater than 1 mM respectively (for example greater than 2 mM respectively). The mixture of free amino acids generated in the hydrolysed preparation according to the invention may comprise a mixture of free amino acids wherein proline is present at a concentration greater than 5 mM.

The food preparation according to the method of the invention may contain flour. In one embodiment, the amount of individual free amino acids in the food preparation according to the method of the invention ranges between 0.001 and 1 parts in weight based on 100 parts of flour. For example, the amount of free amino acids in a food preparation according to the method of the invention may range between 0.005 and 0.1 parts in weight based on 100 parts of flour. The amount of free amino acids in a food preparation according to the method of the invention may range between 0.05 and 0.1 parts in weight based on flour weight.

In an embodiment, the term "heat-treated food product" identifies a product which is dough- or batter-based. The said batter or dough may comprise:
Flour: 100 parts
Water: from 5 to 200 parts
Salts: from 0.1 to 5 parts
Fat: from 0.1 to 100 parts
Eggs: from 0 to 100 parts
Sugar: from 0 to 100 parts
For example, the said batter or dough may comprise:
Flour: 100 parts
Water: from 100 to 180 parts
Salts: from 0 to 5 parts
Fat: from 0.5 to 2 parts
Sugar: from 0 to 5 parts
Particularly when pure enzymes are used, the hydrolysed preparation according to the method of the invention may contain at least a reducing sugar and be the food preparation.

For example, a prolyl endopeptidase and a prolidase comprising an amino acid sequence having at least 95% identity to SEQ ID NO:1 may be added directly to a batter composition as above containing a reducing sugar. When enzymes generated in-situ from microorganisms are used it may be preferable to generate the hydrolysed preparation separately from the main ingredients, for example to better control the growth conditions for the microorganism. In an embodiment, the hydrolysed preparation according to the invention may be incorporated into the food preparation in an amount of from 0.05 to 5 parts in dry weight based on 100 parts of flour. For example, the hydrolysed preparation according to the invention may be incorporated into the food preparation in an amount of from 0.1 to 3 parts in dry weight based on 100 parts of flour.

The hydrolysed preparation according to the method of the invention may be incorporated into the food preparation in an amount of 0.01 to 5 parts by weight of the food preparation. Such levels are appropriate for good flavour generation in the presence of reducing sugars.

In one embodiment, the method of the invention provides a heat-treated food product comprising at least one the of the flavour characteristics: biscuit, buttery, fruity, nutty, caramel, golden syrup, honey, toasted, roasted bread-like and baked. For example, the method of the invention may provide a heat-treated food product comprising a biscuit flavour. In one embodiment, the method of the invention provides a heat-treated food product wherein the heat-treated food product comprises cereal flour (for example wheat flour).

The heat treated food product according to the method of the invention may be selected from the group consisting of biscuit, extruded cereal (for example breakfast cereal), pizza (for example pizza base), beverage powder and caramel.

The biscuit may be a wafer. Wafers are baked products which are made from wafer batter and have crisp, brittle and fragile consistency. They are thin, with an overall thickness usually between <1 and 4 mm and typical product densities range from 0.1 to 0.3 g/cm$^3$. The surfaces are precisely formed, following the surface shape of the plates between which they were baked. They often carry a pattern on one surface or on both. Wafers may also be produced by extrusion. Two basic types of wafer are described by K. F. Tiefenbacher in "Encyclopaedia of Food Science, Food Technology and Nutrition p 417-420—Academic Press Ltd London—1993":

1) No- or low-sugar wafers. The finished biscuits contain from zero to a low percentage of sucrose or other sugars. Typical products are flat and hollow wafer sheets, moulded cones or fancy shapes.
2) High-sugar wafers. More than 10% of sucrose or other sugars are responsible for the plasticity of the freshly baked sheets. They can be formed into different shapes before sugar recrystallization occurs. Typical products are moulded and rolled sugar cones, rolled wafer sticks and deep-formed fancy shapes.

The beverage powder may be a heat-treated milk powder, a cocoa or malt beverage powder or a beverage creamer such as a dairy or non-dairy creamer for use with coffee.

Within the context of the present invention, caramel is a confectionery product made by heating a variety of sugars, for example as sugar syrups in water. Milk ingredients such as skimmed milk powder or condensed milk are typically heated together with the sugar syrups. The caramel may be liquid, or it may have undergone a degree of sugar crystallization to form a solid. It is typically brown in colour and is often found as a filling in chocolate confectionery products.

The edible peptide-containing material according to the method of the invention may be selected from the group consisting of flour (for example wheat flour), milk and peptide-containing components of these, for example gluten (a component of wheat flour) or casein (a component of milk). The edible peptide-containing material according to the method of the invention may be a protein hydrolysate such as a casein hydrolysate.

In an embodiment of the method of the invention the edible peptide-containing material, the prolyl endopeptidase and the prolidase may be contacted in an aqueous dispersion at a temperature of between 30 and 60° C., for example between 45 and 55° C. The edible peptide-containing material, the prolyl endopeptidase and the prolidase may be contacted in an aqueous dispersion at a pH between 5.0 and 8.5.

In an embodiment of the method of the invention the edible peptide-containing material may be contacted with the prolyl endopeptidase and the prolidase sequentially or simultaneously. In the embodiment where the edible peptide-containing material is contacted with the prolyl endopeptidase and prolidase sequentially, then the edible peptide-containing material should be contacted with the prolyl endopeptidase before being contacted with the prolidase. The optimum temperature for contacting the edible peptide-containing material with the prolyl endopeptidase in an aqueous dispersion will depend on exact prolyl endopeptidase selected. In the method of the invention the edible peptide-containing material may be contacted with the prolidase in an aqueous dispersion at a temperature of between 45 and 55° C. The edible peptide-containing material may be contacted with the prolidase in an aqueous dispersion at a pH of between 6.3 and 8.2.

The food preparation may be heated to between 60 and 300° C. during the heat treatment according to the method of the invention. The heat treatment may be selected from the group consisting of pasteurization, sterilization, oven baking, roller drying, and extrusion. The heat treatment may be applied during spray drying.

In a second aspect, the invention provides a hydrolysed preparation obtainable by contacting an edible peptide-containing material with a prolidase, wherein the prolidase comprises an amino acid sequence having at least 95% identity to SEQ ID NO:1. The hydrolysed preparation may be obtainable by contacting an edible peptide-containing material with a prolyl endopeptidase and a prolidase, wherein the prolidase comprises an amino acid sequence having at least 95% identity to SEQ ID NO:1. For example, the prolyl endopeptidase may be contacted with the edible peptide-containing material before, or simultaneously with the prolidase. The molar fraction of proline as a free amino acid may be at least a factor of 2 times higher than in a hydrolysed preparation with the same composition except that the edible peptide-containing material has been completely hydrolysed to free amino acids.

The invention may provide a food preparation incorporating a hydrolysed preparation according to the second aspect of the invention. In a further aspect, the invention provides a food preparation comprising a prolyl endopeptidase, a prolidase, proline as free amino acid and ornithine as a free amino acid; wherein the prolidase comprises an amino acid sequence having at least 95% identity to SEQ ID NO:1; and, if methionine is present as a free amino acid, the molar ratio of proline to methionine as free amino acids is greater than 18. Methionine is responsible for savoury/meaty flavours which are undesirable in many baked goods such as confectionery wafers. The prolyl endopeptidase may for example be a proline-specific endoprotease from *Aspergillus niger*, for example the prolyl endopeptidase may be Maxipro PSP or Maxipro XF from DSM. The invention may provide a heat-treated food product obtainable by heating such a food preparation.

In a still further aspect the invention provides a heat-treated food product obtainable by a method comprising; a) contacting an edible peptide-containing material with a prolidase to form a hydrolysed preparation, wherein the prolidase comprises an amino acid sequence having at least 95% identity to SEQ ID NO:1; b) incorporating the hydrolysed preparation obtainable from step (a) into a food preparation which comprises at least a reducing sugar; or, where the hydrolysed preparation already comprises at least a reducing sugar, the hydrolysed preparation may be the food preparation; and c) subjecting the food preparation to heat treatment to obtain a heat-treated food product. The heat-treated food product may be obtainable by a method comprising; a) contacting an edible peptide-containing material with a prolyl endopeptidase and a prolidase to form a hydrolysed preparation, wherein the prolidase comprises an amino acid sequence having at least 95% identity to SEQ ID NO:1; b) incorporating the hydrolysed preparation obtainable from step (a) into a food preparation which comprises at least a reducing sugar; or, where the hydrolysed preparation already comprises at least a reducing sugar, the hydrolysed preparation may be the food preparation; and c) subjecting the food preparation to heat treatment to obtain a heat-treated food product.

In a still further aspect, the invention provides for the use of a prolidase comprising an amino acid sequence having at least 95% identity to SEQ ID NO:1 to improve the flavour of a heat-treated food product. The prolidase may be used in combination with a prolyl endopeptidase, for example the prolidase may be used after or simultaneously with a prolyl endopeptidase.

Those skilled in the art will understand that they can freely combine all features of the present invention disclosed herein. In particular, features described for the method of the present invention may be combined with the product of the present invention and vice versa. Further, features described for different embodiments of the present invention may be combined. Where known equivalents exist to specific features, such equivalents are incorporated as if specifically referred to in this specification.

Further advantages and features of the present invention are apparent from the figures and non-limiting examples.

EXAMPLES

Example 1: Generation of Amino Acids with Prolyl Endopeptidase and *Saccharomyces Cerevisiae* Prolidase Prolidase enzyme from *Saccharomyces cerevisiae* having the SEQ ID NO:1 was expressed (Biocatalysts Ltd. UK). A 10% w/v suspension of wheat gluten was incubated for 10 min at 50° C. and pH 5.5 with $0.4\%_{vs\ prot.}$ prolyl endopeptidase (Maxipro XF from DSM). Then the pH was increased to 7.2, $1.0\%_{prot.\ vs\ prot.}$ of prolidase from *S. cerevisiae* was added and the mixture was again incubated for 24 hours at 50° C. For comparison, wheat gluten was treated under the same pH and incubation conditions but only using the prolyl endopeptidase.

Figure 1:
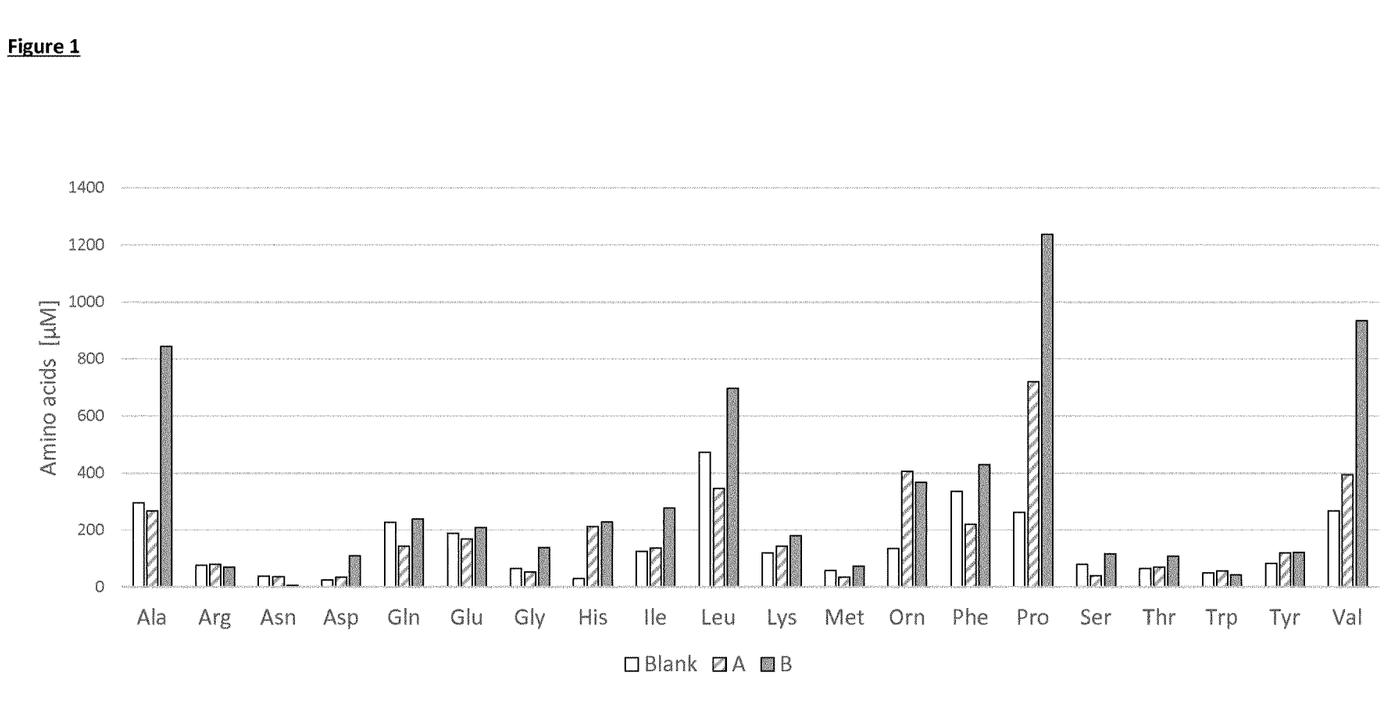
FIG. 1 is a plot of free amino acid quantity (μM) in unreacted wheat gluten (Blank), wheat gluten reacted with prolyl endopeptidase and *Saccharomyces cerevisiae* prolidase (B) and wheat gluten with prolyl endopeptidase alone (A). The amino acids are Alanine (ala), Arginine (arg), Asparagine (asn), Aspartic acid (asp), Glutamine (gin), Glutamic acid (glu), Glycine (gly), Histidine (his), Isoleucine (ile), Leucine (leu), Lysine (lys), Methionine (met), Ornithine (orn), Phenylalanine (phe), Proline (pro), Serine (ser), Threonine (thr), Tryptophan (trp), Tyrosine (tyr), Valine (val).

The determination of amino acids was performed using a Nucleodur 100-3 HILIC column. Amino acids were eluted with a gradient of water in acetonitrile, both containing 0.5% acetic acid. The detection is perfomed using a Triple Quadropole (QQQ) Mass Spectrometer. Different dilutions of standard solutions were used to determine linear regressions of the ratio between the peak area of each amino acid versus the peak area of the corresponding deuterated amino acid as a function of concentration. The quantities of amino acids obtained are plotted in FIG. 1, the unreacted wheat gluten is also shown (Blank). It can be seen that contacting the wheat gluten with prolyl endopeptidase and the prolidase from *S. cerevisiae* (B) provides a greater yield of proline than using prolyl endopeptidase alone (A).

Example 2: Comparison with Prolyl Endopeptidase/Carboxypeptidase CPD-Y

The combination prolyl endopeptidase/*S. cerevisiae* prolidase was compared with using the combination proposed in WO2005/117595; prolyl endopeptidase/carboxypeptidase CPD-Y. Initially a 49% w/v suspension of wheat flour (corresponding to a 10% w/v suspension of wheat gluten) was incubated for 2 hours at 50° C. and pH 5.0 with $0.4\%_{vs\ prot.}$ prolyl endopeptidase (Maxipro XF) and $0.1\%_{prot.\ vs\ prot.}$ of either the carboxypeptidase CPD-Y (Sigma), or prolidase from *S. cerevisiae* as in Example 1. The activity of carboxypeptidase CPD-Y was found not to be the same as prolidase from *S. cerevisiae* (carboxypeptidase CPD-Y has an overall higher activity) so, to evaluate the selectivity of the enzymes, further experiments were performed with similar extents of conversion, the amount of CPD-Y being reduced compared to the prolidase from *S. cerevisiae*.

Figure 2:
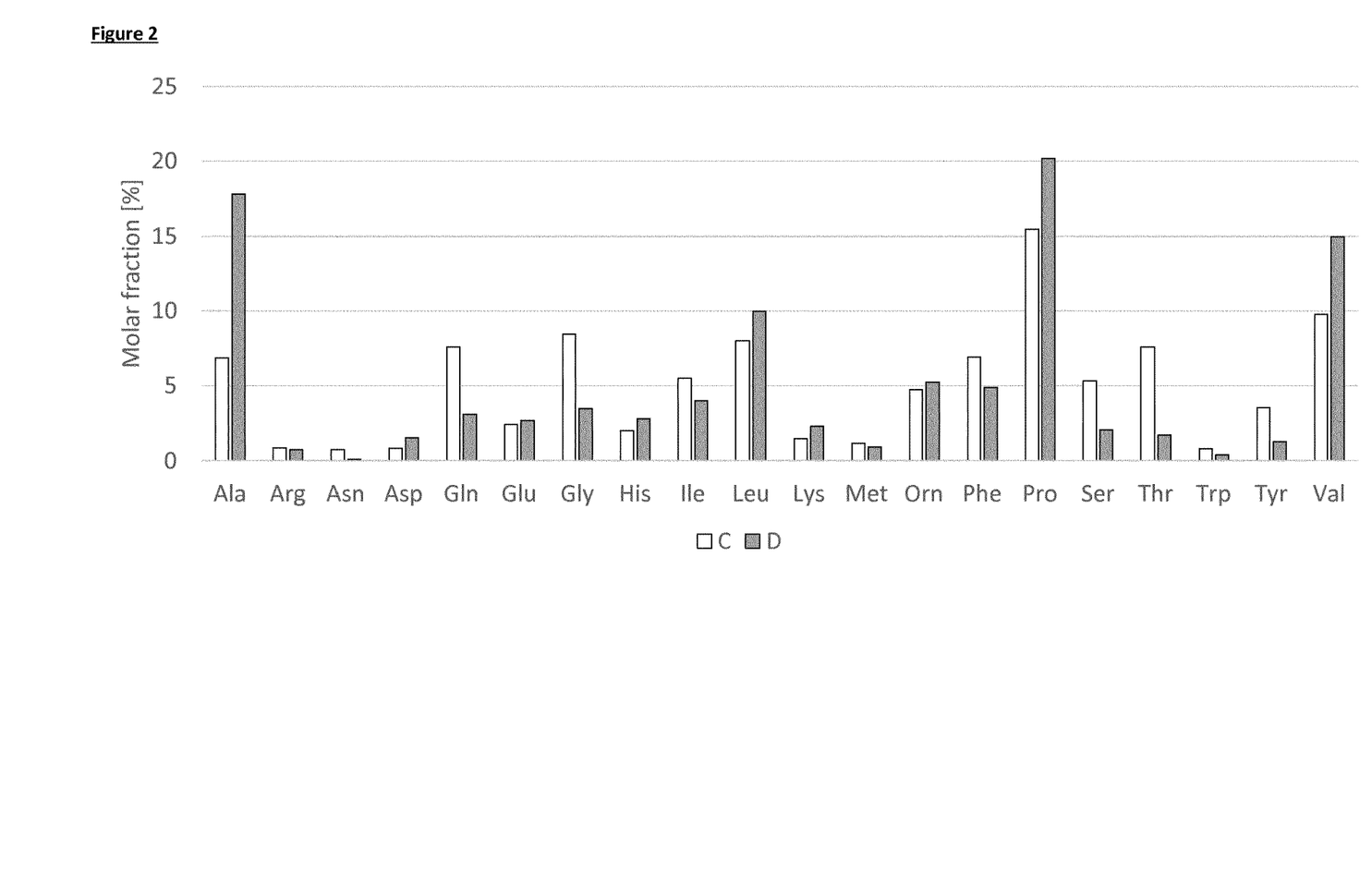
FIG. 2 is a plot of free amino acid molar fractions for wheat gluten incubated with prolyl endopeptidase and CPD-Y prolidase (C) or prolyl endopeptidase and *S. cerevisiae* prolidase (D).

A 10% w/v suspension of wheat gluten was incubated for 10 min at 50° C. and pH 5.5 with $0.4\%_{vs\ prot.}$ proline specific endopeptidase (Maxipro XF) before being hydrolysed with either $1.0\%_{prot.\ vs\ prot.}$ of prolidase from *S. cerevisiae* or $0.1\%_{prot.\ vs\ prot.}$ of CPD-Y. The pH was increased to 7.2 and the mixture was incubated for about 24 hours at 50° C. The free amino acids produced are shown in FIG. 2. The amounts of amino acids are given as molar fractions. The molar fraction represents the proportion of one individual amino acid versus the sum of all free amino acids present after enzymatic hydrolysis. It is a simple way to illustrate the selectivity of the enzyme. It can be seen that prolidase from *S. cerevisiae* (D) has a much greater specificity for proline production than CPD-Y (C). This is beneficial, as proline generates attractive baked flavours in the Maillard reaction. In addition, prolidase from *S. cerevisiae* produced less methionine than CPD-Y. Methionine is responsible for savoury/meaty flavours which are undesirable in many baked goods such as confectionery wafers. The ratio of praline to methionine was 13.4 for CPD-Y, but was 22.9 for the *S. cerevisiae* prolidase.

Example 3: Heat Induced Lysis of *S. cerevisiae*

Casein peptone (CP) medium was prepared by dissolving 10 g of yeast extract, 20 g of casein peptone and 20 g of dextrose per litre of water. The solution had a pH around 6.5 and was further sterilized by filtration through 0.2 μm filter. *S. cerevisiae* yeast (temperature sensitive strain CNCM I-4006) was cultivated in the CP medium. An inoculum was prepared from glycerol stock of the yeast strain stored at −80° C. A first culture was carried out inoculating 10 mL of fresh CP medium with 2% of the strain stock. Afterwards, a second culture was performed, inoculating 10 mL of fresh CP medium with 2% of the first culture. The broth was then incubated in a shaker for 24 h at 25° C. and 130 rpm, under aerobic conditions. Fermentation was performed in small fermenter containing CP medium under the following conditions; inoculation 1% v/v, temperature 25° C., aerobic condition controlling the dissolved oxygen at a minimum level of 30%.

Depletion of sugars in the growth medium reflects the depletion of nutrients in the growth medium and indicates the end of microorganism growth. Sugars were determined by HPLC, combining ion exclusion and partition (column Aminex HPX-87H, 300×7.8 mm). Sugars were eluted with 0.6 mL/min 5 mM sulfuric acid and detected using a refractive index detector. Different dilutions of standard solutions were used to determine linear regressions of peak area as a function of the concentration.

Microorganism cell autolysis is indirectly measured on the basis of enumeration of viable microorganism cells in the growth medium. The method used was to count the number of Colony Forming Units per millilitre (cfu/mL) of fermentation broth. Serial dilutions of the sample were used to find the appropriate concentration where every single viable cell is isolated from the others. Diluent was composed of 1 g tryptone and 8.5 g sodium chloride per litre of water. Aliquots of different dilutions (20 µL) were then deposited onto an YPD (Yeast peptone dextrose) agar plate. After drying, the plates were incubated at 30° C. for 48 h. Each of the previous steps was performed in sterile conditions. Finally, the colonies were counted and viable cells count calculated using the equation:

Viable cells count=$N \times 50 \times D$

Where N is the number of colonies in the selected spot and D is the dilution factor.

Figure 3:
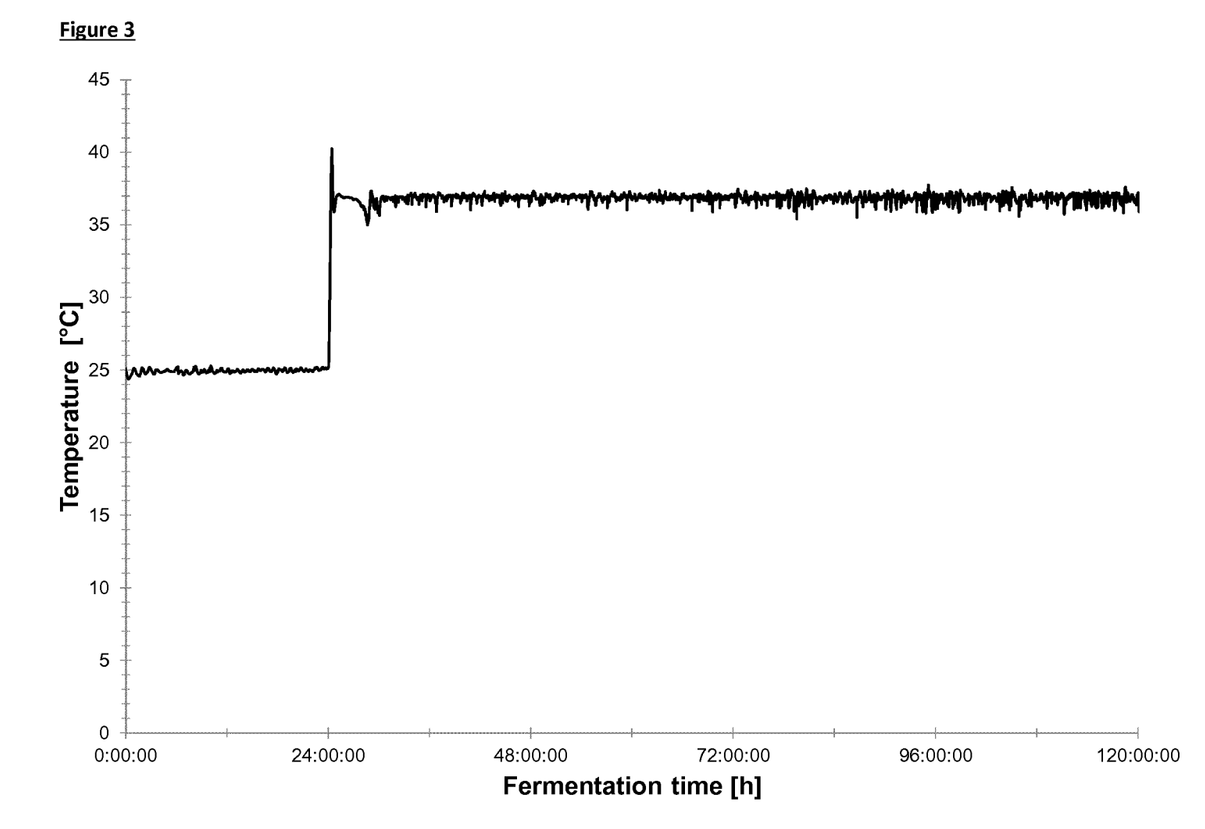
FIG. 3 shows a graph representing the temperature profile during cultivation of *S. cerevisiae* cells in CP medium as a result of experiments described in Example 3.

Initial measured pH for the growth medium during cultivation of *S. cerevisiae* yeast (temperature sensitive strain CNCM I-4006) was around 6.5. Maximal growth was obtained within 24 h when glucose was completely depleted (see FIG. 4). At 24 h, glucose was added to the medium, up to a concentration of 350 mM within 4 hours. At the same time, temperature was increased from 25 to 37° C. (see FIG. 3)

Figure 4:
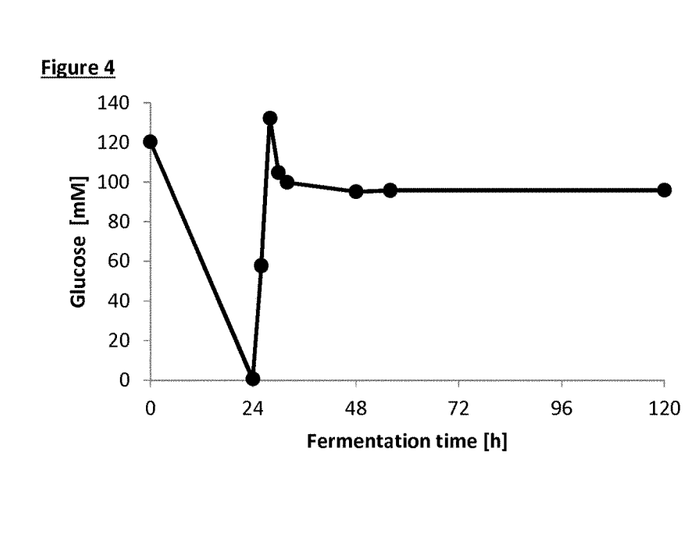
FIG. 4 shows the residual glucose during cultivation of *S. cerevisiae* cells in casein peptone medium as a result of experiments described in Example 3.

Glucose was totally consumed during the growth phase and about 250 mM of the added glucose was consumed during the lysis (see FIG. 4).

Figure 5:
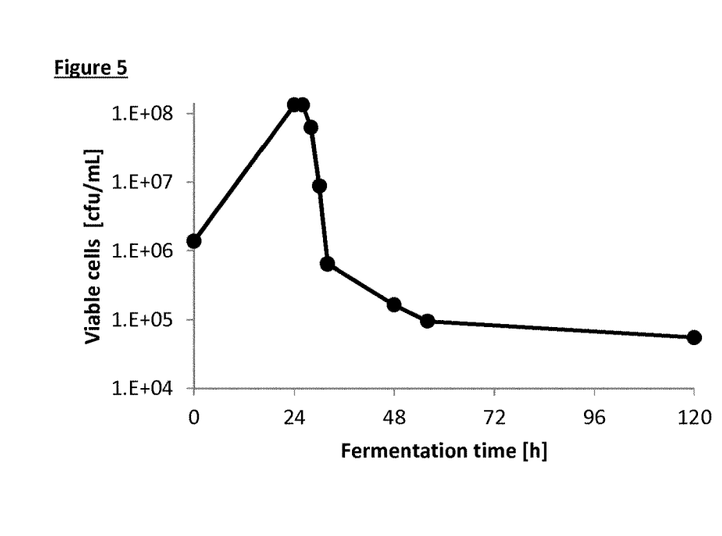
FIG. 5 shows the viability of *S. cerevisiae* cells (cfu/mL) against fermentation time (h) on casein peptone medium as a result of experiments described in Example 3.

The viability of *S. cerevisiae* cells dropped as soon as the cells tried to grow again when sugar was added. Without wishing to be bound by theory, it is believed that the increase in temperature prevents performing a normal division of the cells resulting in their lysis (see FIG. 5).

Figure 6:
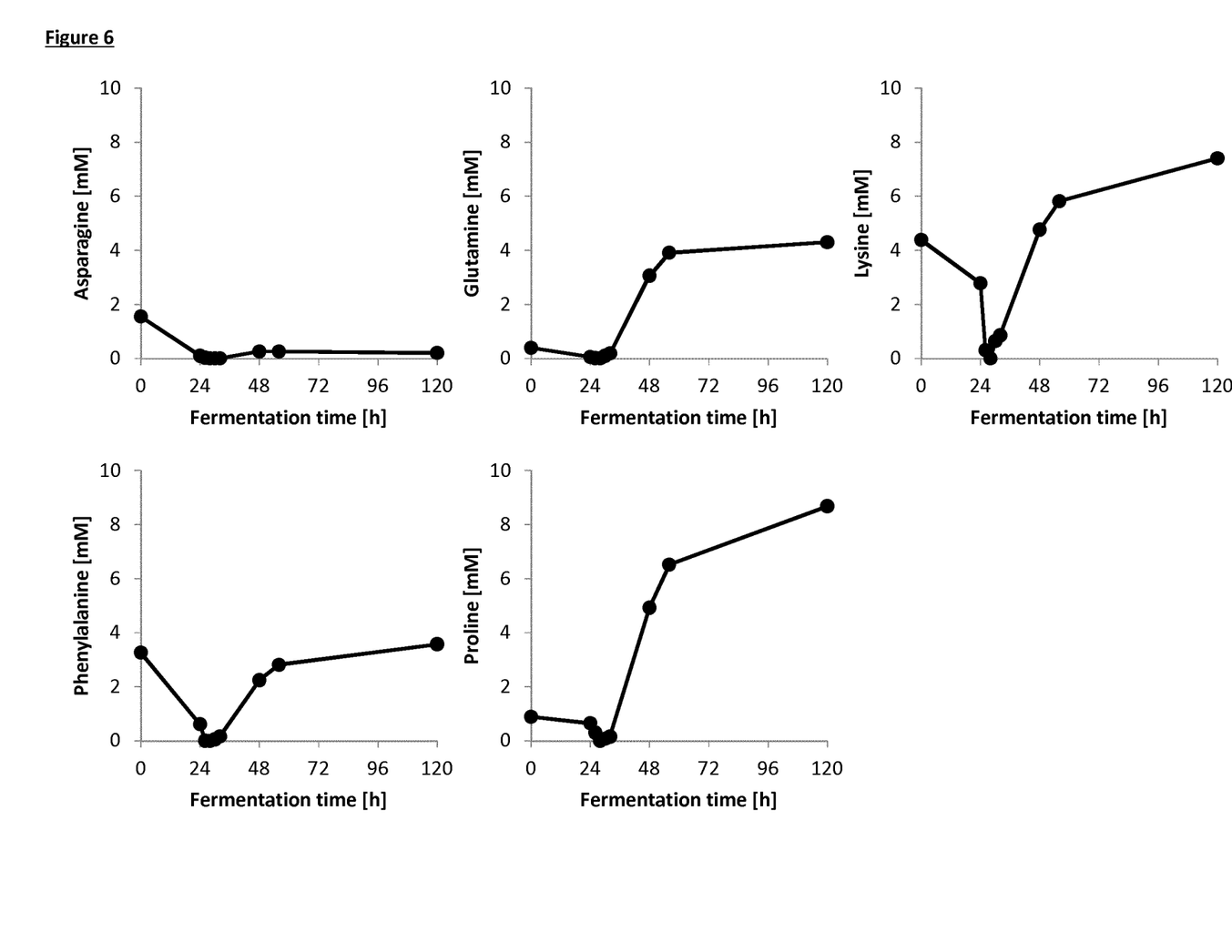
FIG. 6 shows the release of selected free amino acids [mM concentration] during *S. cerevisiae* fermentation in casein peptone medium as a result of experiments described in Example 3.
Figure 7:
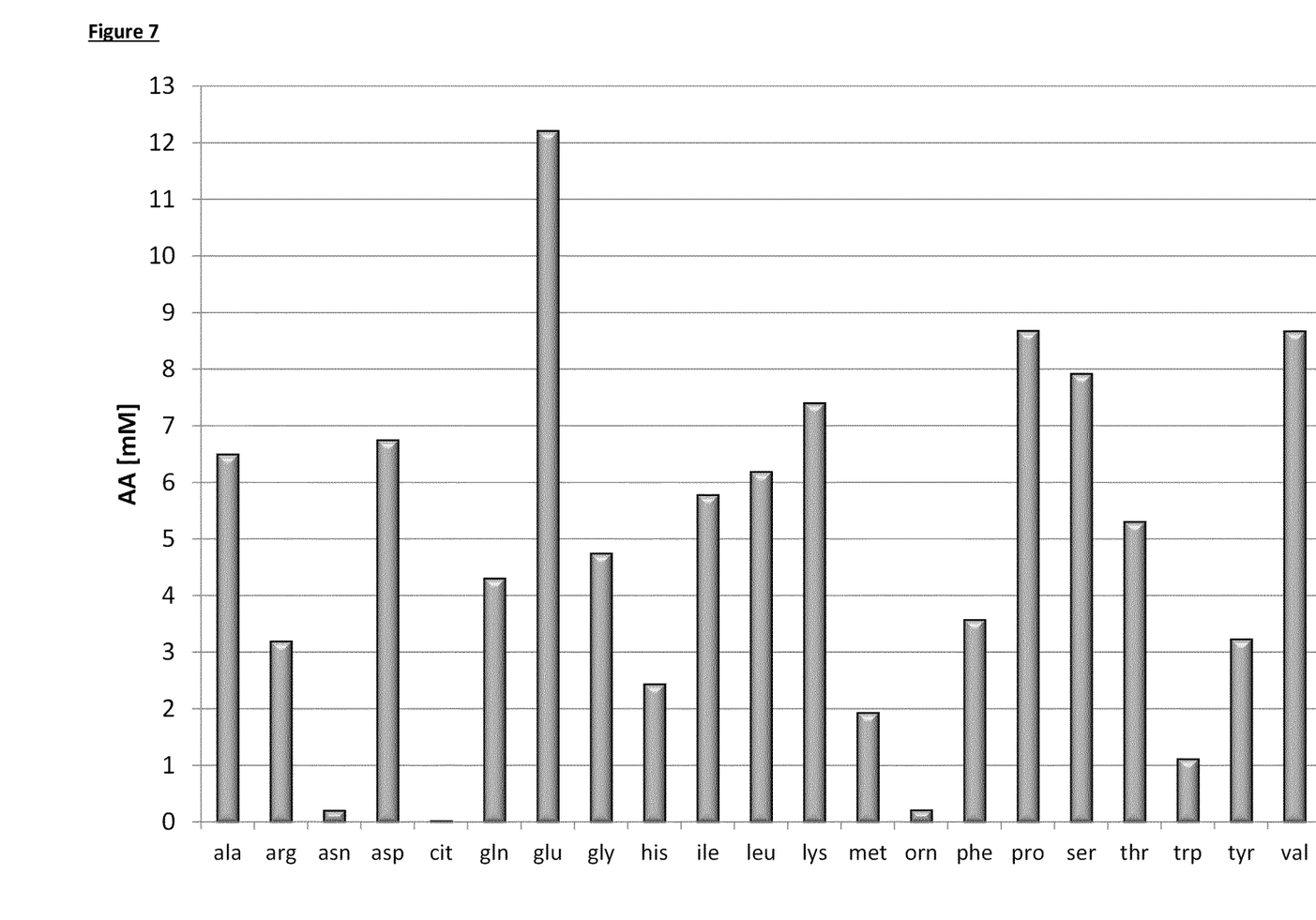
FIG. 7 shows a graph representing the free amino acid concentration [mM] obtained after 5 days of fermentation as a result of experiments described in Example 3. The amino acids are Alanine (ala), Arginine (arg), Asparagine (asn), Aspartic acid (asp), Cittruline (cit), Glutamine (gin), Glutamic acid (glu), Glycine (gly), Histidine (his), Isoleucine (ile), Leucine (leu), Lysine (lys), Methionine (met), Ornithine (orn), Phenylalanine (phe), Proline (pro), Serine (ser), Threonine (thr), Tryptophan (trp), Tyrosine (tyr), Valine (val).

The amount of free amino acids present in the fermentation medium were measured at different times (determination method as in example 1). Results for selected free amino acids are reported in FIG. 6 (time course of amount developed for Asparagine, Glutamine, Lysine, Ornithine, Phenylalanine and Proline). The measured final concentrations [mM] in the fermentation medium for all the released amino acids is reported in FIG. 7.

Free amino acids that were initially present in CP medium were totally consumed during the growth of strain CNCM I-4006. As soon as the cells lysed and pH was increased to 7 by addition of NaOH aq solution 2M, hydrolysis of proteins and peptides from casein peptone and yeast extract started with associated release of free amino acids (see FIGS. 6 and 7), proline being the second most abundant.

Thanks to the levels of free amino acids developed, the fermented preparation according to the invention may be incorporated into a food preparation comprising at least a reducing sugar to achieve development of appropriate flavours on heat treatment as a consequence of Maillard reactions.

It can be seen that *S. cerevisiae* lyses upon application of heat and releases prolidase enzymes.

The invention claimed is:

1. A method for flavor generation, the method comprising:
   (a) contacting (1) gluten with (2) a prolyl-specific endopeptidase from *Aspergillus niger* and (3) a prolidase, at a pH from 5.5 to 7.2 to form a hydrolysed preparation, wherein the prolidase comprises the amino acid sequence SEQ ID NO:1; and
   (b) subjecting a food preparation comprising the hydrolysed preparation to heat treatment to obtain a heat-treated food product, wherein the food preparation comprises a reducing sugar that was present in the hydrolysed preparation or added to the hydrolysed preparation, and the prolidase is obtained from *Saccharomyces cerevisiae*.

2. The method according to claim 1, wherein the prolidase is obtained by lysis of *Saccharomyces cerevisiae*.

3. The method according to claim 1, wherein the reducing sugar is rhamnose.

4. The method according to claim 1, wherein the hydrolysed preparation is incorporated into the food preparation in an amount of 0.01 to 5 parts by weight of the food preparation.

5. The method according to claim 1, wherein the heat-treated food product is selected from the group consisting of biscuit, extruded cereal, pizza, beverage powder and caramel.

6. The method according to claim 1, wherein (1) the gluten, (2) the prolyl-specific endopeptidase from *Aspergillus niger*, and (3) the prolidase are contacted in an aqueous dispersion at a temperature of between 30 and 60° C.

7. The method according to claim 1, wherein (1) the gluten is contacted with (3) the prolidase in an aqueous dispersion at a temperature of 45-55° C.

8. The method according to claim 1, wherein (1) the gluten is contacted with (3) the prolidase in an aqueous dispersion at a pH between 6.3 and 7.2.

\* \* \* \* \*

SEQUENCE LISTING

<160> NUMBER OF SEQ ID NOS: 1

<210> SEQ ID NO 1
<211> LENGTH: 481
<212> TYPE: PRT
<213> ORGANISM: Saccharomyces cerevisiae

<400> SEQUENCE: 1

```
Met Ser His Ser Leu Thr Ser Val Phe Gln Lys Ile Asp Ser Leu Lys
1               5                   10                  15

Pro Gln Phe Phe Ser Arg Leu Thr Lys Ala Ile Gln Ile Pro Ala Val
            20                  25                  30

Ser Ser Asp Glu Ser Leu Arg Ser Lys Val Phe Asp Lys Ala Lys Phe
        35                  40                  45

Ile Ser Glu Gln Leu Ser Gln Ser Gly Phe His Asp Ile Lys Met Val
    50                  55                  60

Asp Leu Gly Ile Gln Pro Pro Ile Ser Thr Pro Asn Leu Ser Leu
65                  70                  75                  80

Pro Pro Val Ile Leu Ser Arg Phe Gly Ser Asp Pro Ser Lys Lys Thr
                85                  90                  95

Val Leu Val Tyr Gly His Tyr Asp Val Gln Pro Ala Gln Leu Glu Asp
            100                 105                 110

Gly Trp Asp Thr Glu Pro Phe Lys Leu Val Ile Asp Glu Ala Lys Gly
```

```
              115                 120                 125
Ile Met Lys Gly Arg Gly Val Thr Asp Asp Thr Gly Pro Leu Leu Ser
    130                 135                 140

Trp Ile Asn Val Val Asp Ala Phe Lys Ala Ser Gly Gln Glu Phe Pro
145                 150                 155                 160

Val Asn Leu Val Thr Cys Phe Glu Gly Met Glu Glu Ser Gly Ser Leu
                165                 170                 175

Lys Leu Asp Glu Leu Ile Lys Lys Glu Ala Asn Gly Tyr Phe Lys Gly
            180                 185                 190

Val Asp Ala Val Cys Ile Ser Asp Asn Tyr Trp Leu Gly Thr Lys Lys
        195                 200                 205

Pro Val Leu Thr Tyr Gly Leu Arg Gly Cys Asn Tyr Tyr Gln Thr Ile
    210                 215                 220

Ile Glu Gly Pro Ser Ala Asp Leu His Ser Gly Ile Phe Gly Gly Val
225                 230                 235                 240

Val Ala Glu Pro Met Ile Asp Leu Met Gln Val Leu Gly Ser Leu Val
                245                 250                 255

Asp Ser Lys Gly Lys Ile Leu Ile Asp Gly Ile Asp Glu Met Val Ala
            260                 265                 270

Pro Leu Thr Glu Lys Glu Lys Ala Leu Tyr Lys Asp Ile Glu Phe Ser
        275                 280                 285

Val Glu Glu Leu Asn Ala Ala Thr Gly Ser Lys Thr Ser Leu Tyr Asp
    290                 295                 300

Lys Lys Glu Asp Ile Leu Met His Arg Trp Arg Tyr Pro Ser Leu Ser
305                 310                 315                 320

Ile His Gly Val Glu Gly Ala Phe Ser Ala Gln Gly Ala Lys Thr Val
                325                 330                 335

Ile Pro Ala Lys Val Phe Gly Lys Phe Ser Ile Arg Thr Val Pro Asp
            340                 345                 350

Met Asp Ser Glu Lys Leu Thr Ser Leu Val Gln Lys His Cys Asp Ala
        355                 360                 365

Lys Phe Lys Ser Leu Asn Ser Pro Asn Lys Cys Arg Thr Glu Leu Ile
    370                 375                 380

His Asp Gly Ala Tyr Trp Val Ser Asp Pro Phe Asn Ala Gln Phe Thr
385                 390                 395                 400

Ala Ala Lys Lys Ala Thr Lys Leu Val Tyr Gly Val Asp Pro Asp Phe
                405                 410                 415

Thr Arg Glu Gly Gly Ser Ile Pro Ile Thr Leu Thr Phe Gln Asp Ala
            420                 425                 430

Leu Asn Thr Ser Val Leu Leu Pro Met Gly Arg Gly Asp Asp Gly
        435                 440                 445

Ala His Ser Ile Asn Glu Lys Leu Asp Ile Ser Asn Phe Val Gly Gly
    450                 455                 460

Met Lys Thr Met Ala Ala Tyr Leu Gln Tyr Tyr Ser Glu Ser Pro Glu
465                 470                 475                 480

Asn
```